United States Patent
Jackowski et al.

(10) Patent No.: US 7,049,397 B2
(45) Date of Patent: May 23, 2006

(54) BIOPOLYMER MARKER INDICATIVE OF DISEASE STATE HAVING A MOLECULAR WEIGHT OF 1211 DALTONS

(75) Inventors: George Jackowski, Kettleby (CA); Brad Thatcher, Toronto (CA); John Marshall, Toronto (CA); Jason Yantha, Toronto (CA); Tammy Vrees, Oakville (CA)

(73) Assignee: Syn X Pharma, Inc., Ontario (CA)

( * ) Notice: Subject to any disclaimer, the term of this patent is extended or adjusted under 35 U.S.C. 154(b) by 0 days.

(21) Appl. No.: 09/845,731

(22) Filed: Apr. 30, 2001

(65) Prior Publication Data

US 2003/0004307 A1    Jan. 2, 2003

(51) Int. Cl.
C07K 7/06 (2006.01)
G01N 33/53 (2006.01)

(52) U.S. Cl. .................. 530/328; 435/7.1; 436/173; 702/23

(58) Field of Classification Search .............. 530/300, 530/328; 435/7.1; 424/9.1; 702/23; 436/173
See application file for complete search history.

(56) References Cited

U.S. PATENT DOCUMENTS

| | | | |
|---|---|---|---|
| 5,062,935 A | 11/1991 | Schlag et al. | 204/157 |
| 5,538,897 A | 7/1996 | Yates, III et al. | 436/89 |
| 6,020,208 A | 2/2000 | Hutchens et al. | 436/174 |

FOREIGN PATENT DOCUMENTS

| | | |
|---|---|---|
| WO | WO 87/06344 | 10/1987 |
| WO | WO 90/14148 | 11/1990 |
| WO | WO 91/13352 | 9/1991 |
| WO | WO 93/24834 | 12/1993 |
| WO | WO 98/07036 | 2/1998 |
| WO | WO 98/32390 | 7/1998 |
| WO | WO 00/49410 | 8/2000 |
| WO | WO 01/05422 | 1/2001 |

OTHER PUBLICATIONS

Richter et al, Composition of the peptide fraction in human blood plasma: database of circulating human peptides, J. Chrom. B. Biomed. Sci. Appl., 726, 1-2, (1999), pp. 25-35.

(Continued)

Primary Examiner—Marjorie A. Moran
Assistant Examiner—Carolyn L. Smith
(74) Attorney, Agent, or Firm—McHale & Slavin, P.A.

(57) ABSTRACT

The instant invention involves the use of a combination of preparatory steps in conjunction with mass spectroscopy and time-of-flight detection procedures to maximize the diversity of biopolymers which are verifiable within a particular sample. The cohort of biopolymers verified within such a sample is then viewed with reference to their ability to evidence at least one particular disease state; thereby enabling a diagnostician to gain the ability to characterize either the presence or absence of said at least one disease state relative to recognition of the presence and/or the absence of said biopolymer.

9 Claims, 2 Drawing Sheets

Biopolymer Indicative of Disease State - MW 1211

| Code # | Gender | Age | Patient History | Disease | MW | Protein Name | Sequence |
|---|---|---|---|---|---|---|---|
| SJ CON 06 | F | 77 | | MI | 1211 | Complement C3f | (H)RIHWESASLL(R) |
| SJ CON 07 | M | 65 | GE (gastroesophageal) reflux | MI | 1211 | Complement C3f | (H)RIHWESASLL(R) |
| SJ CON 10 | F | 50 | Inferior MI, Hiatal Hernia | MI | 1211 | Complement C3f | (H)RIHWESASLL(R) |
| SJ CON 14 | F | 65 | MI, NIDDM | MI | 1211 | Complement C3f | (H)RIHWESASLL(R) |
| SJ CON 17 | M | 58 | | MI | 1211 | Complement C3f | (H)RIHWESASLL(R) |
| SJ CON 19 | M | 52 | | MI | 1211 | Complement C3f | (H)RIHWESASLL(R) |
| SJ CON 21 | M | 65 | | MI | 1211 | Complement C3f | (H)RIHWESASLL(R) |
| HNS-SJ22 | | | | MI | 1211 | Complement C3f | (H)RIHWESASLL(R) |
| HNS-SJ28 | | | | MI | 1211 | Complement C3f | (H)RIHWESASLL(R) |
| HNS-SJ33 | | | | MI | 1211 | Complement C3f | (H)RIHWESASLL(R) |
| CU-15 | F | 54 | Acute CVA, Basal ganglia | Stroke-ICH | 1211 | Complement C3f | (H)RIHWESASLL(R) |
| CU-18 | M | 72 | HTN, previous CVA, CVA (R MCA) used tP | Stroke-ICH | 1211 | Complement C3f | (H)RIHWESASLL(R) |
| CU-19 | M | 47 | CVA, transfer to VA | Stroke-ICH | 1211 | Complement C3f | (H)RIHWESASLL(R) |
| CU-30 | M | 55 | HTN, ICH | Stroke-ICH | 1211 | Complement C3f | (H)RIHWESASLL(R) |
| CU-33 | M | 72 | Prior CVA, acute CVA (L MCA) | Stroke-ICH | 1211 | Complement C3f | (H)RIHWESASLL(R) |
| CU-37 | M | 72 | HTN, acute CVA (R subcortical | Stroke-ICH | 1211 | Complement C3f | (H)RIHWESASLL(R) |
| CU-38 | F | 67 | HTN, Diabetes, acute CVA (R parietal) | Stroke-ICH | 1211 | Complement C3f | (H)RIHWESASLL(R) |
| 23604 - KKB | M | 61 | STAGE 3 | CHF | 1211 | Complement C3f | (H)RIHWESASLL(R) |
| 23707 - KL | F | 65 | STAGE 3 | CHF | 1211 | Complement C3f | (H)RIHWESASLL(R) |
| 22703 - MM | F | 87 | STAGE 3 | CHF | 1211 | Complement C3f | (H)RIHWESASLL(R) |
| 20206 - MM | F | 75 | STAGE 4 | CHF | 1211 | Complement C3f | (H)RIHWESASLL(R) |
| 22103 - GM | F | 77 | STAGE 3 | CHF | 1211 | Complement C3f | (H)RIHWESASLL(R) |
| 21813 - GR | F | 65 | STAGE 3 | CHF | 1211 | Complement C3f | (H)RIHWESASLL(R) |
| 23008 - GFB | M | 67 | STAGE3 - DEAD | CHF | 1211 | Complement C3f | (H)RIHWESASLL(R) |
| 23402 - HM | M | 67 | STAGE 3 | CHF | 1211 | Complement C3f | (H)RIHWESASLL(R) |
| 20208 - HIF | M | 79 | STAGE 3 | CHF | 1211 | Complement C3f | (H)RIHWESASLL(R) |
| 22803 - HB | M | 60 | STAGE 3 | CHF | 1211 | Complement C3f | (H)RIHWESASLL(R) |
| 23616 - JGK | M | 43 | STAGE 3 | CHF | 1211 | Complement C3f | (H)RIHWESASLL(R) |
| 20803 - EW | M | 45 | Acute MI - STAGE 3 | CHF | 1211 | Complement C3f | (H)RIHWESASLL(R) |
| 23421 - FB | M | 59 | STAGE 3 | CHF | 1211 | Complement C3f | (H)RIHWESASLL(R) |
| 22813 - CL | F | 66 | STAGE 4 | CHF | 1211 | Complement C3f | (H)RIHWESASLL(R) |
| 23130 - ER | M | 51 | STAGE 3 | CHF | 1211 | Complement C3f | (H)RIHWESASLL(R) |
| 23105 - FC | M | 64 | STAGE 3 | CHF | 1211 | Complement C3f | (H)RIHWESASLL(R) |
| 23116 - FC | M | 59 | STAGE 3 | CHF | 1211 | Complement C3f | (H)RIHWESASLL(R) |
| 20414 - EYG | F | 76 | STAGE 3 | CHF | 1211 | Complement C3f | (H)RIHWESASLL(R) |
| 23130 - ER | M | 51 | STAGE 3 | CHF | 1211 | Complement C3f | (H)RIHWESASLL(R) |
| 23134 - FC | M | 62 | STAGE 3 | CHF | 1211 | Complement C3f | (H)RIHWESASLL(R) |
| 20102 - EAB | M | 70 | STAGE 3 | CHF | 1211 | Complement C3f | (H)RIHWESASLL(R) |

OTHER PUBLICATIONS

Takahashi et al, Rapid and sensitive immunoassay for the measurement of serum S100B using isoform-specific monoclonal antibody, Clin. Chem., 45, 8, (1999), pp. 1307-1311.

Tang, et al., "Contribution of Renal Secreted Completed C3 to the Circulating Pool in Humans[1]", Journal of Immunology (1999), vol. 162, No. 7, pp. 4336-4341.

Koch, et al., "A Novel Polymorphism of Human Complement Component C3 Detected by Means of a Monoclonal Antibody", Immunogenetics (1986), vol. 23, No. 5, pp. 322-325.

Muscari, et al., "Association of Serum C3 Levels With the Risk of Myocardial Infarction", American Journal of Medicine (1995), vol. 98, No. 4, pp. 357-364.

Harrison et al., "Structure of C3f, a Small Peptide Specifically Released during Inactivation of the Third Component of Complement", Component (1988), vol. 5, No. 1, pp. 27-32.

Figure 1
Biopolymer Indicative of Disease State - MW 1211

| Code # | Gender | Age | Patient History | Disease | MW | Protein Name | Sequence |
|---|---|---|---|---|---|---|---|
| SJ CON 06 | F | 77 | | MI | 1211 | Complement C3f | (H)RIHWESASLL(R) |
| SJ CON 07 | M | 65 | GE (gastroesophageal) reflux | MI | 1211 | Complement C3f | (H)RIHWESASLL(R) |
| SJ CON 10 | F | 50 | Inferior MI, Hiatal Hernia | MI | 1211 | Complement C3f | (H)RIHWESASLL(R) |
| SJ CON 14 | F | 65 | MI, NIDDM | MI | 1211 | Complement C3f | (H)RIHWESASLL(R) |
| SJ CON 17 | M | 58 | | MI | 1211 | Complement C3f | (H)RIHWESASLL(R) |
| SJ CON 19 | M | 52 | | MI | 1211 | Complement C3f | (H)RIHWESASLL(R) |
| SJ CON 21 | M | 65 | | MI | 1211 | Complement C3f | (H)RIHWESASLL(R) |
| HNS-SJ22 | | | | MI | 1211 | Complement C3f | (H)RIHWESASLL(R) |
| HNS-SJ28 | | | | MI | 1211 | Complement C3f | (H)RIHWESASLL(R) |
| HNS-SJ33 | | | | MI | 1211 | Complement C3f | (H)RIHWESASLL(R) |
| CU-15 | F | 54 | Acute CVA, Basal ganglia | Stroke-ICH | 1211 | Complement C3f | (H)RIHWESASLL(R) |
| CU-18 | M | 72 | HTN, previous CVA, CVA (R MCA) used tP | Stroke-ICH | 1211 | Complement C3f | (H)RIHWESASLL(R) |
| CU-19 | M | 47 | CVA, transfer to VA | Stroke-ICH | 1211 | Complement C3f | (H)RIHWESASLL(R) |
| CU-30 | M | 56 | HTN, ICH | Stroke-ICH | 1211 | Complement C3f | (H)RIHWESASLL(R) |
| CU-33 | M | 72 | Prior CVA, acute CVA (L MCA) | Stroke-ICH | 1211 | Complement C3f | (H)RIHWESASLL(R) |
| CU-37 | M | 72 | HTN, acute CVA (R subcortical | Stroke-ICH | 1211 | Complement C3f | (H)RIHWESASLL(R) |
| CU-38 | F | 67 | HTN, Diabetes, acute CVA (R parietal) | Stroke-ICH | 1211 | Complement C3f | (H)RIHWESASLL(R) |
| 23604 - KKB | M | 61 | STAGE 3 | CHF | 1211 | Complement C3f | (H)RIHWESASLL(R) |
| 23707 - KL | F | 65 | STAGE 3 | CHF | 1211 | Complement C3f | (H)RIHWESASLL(R) |
| 22703 - MM | F | 67 | STAGE 3 | CHF | 1211 | Complement C3f | (H)RIHWESASLL(R) |
| 20206 - MM | F | 75 | STAGE 4 | CHF | 1211 | Complement C3f | (H)RIHWESASLL(R) |
| 22103 - GM | F | 77 | STAGE 3 | CHF | 1211 | Complement C3f | (H)RIHWESASLL(R) |
| 21813 - GR | F | 65 | STAGE 3 | CHF | 1211 | Complement C3f | (H)RIHWESASLL(R) |
| 23008 - GFB | M | 67 | STAGE3 - DEAD | CHF | 1211 | Complement C3f | (H)RIHWESASLL(R) |
| 23402 - HM | M | 67 | STAGE 3 | CHF | 1211 | Complement C3f | (H)RIHWESASLL(R) |
| 20208 - HIF | M | 79 | STAGE 3 | CHF | 1211 | Complement C3f | (H)RIHWESASLL(R) |
| 22803 - HB | M | 60 | STAGE 3 | CHF | 1211 | Complement C3f | (H)RIHWESASLL(R) |
| 23616 - JGK | M | 43 | STAGE 3 | CHF | 1211 | Complement C3f | (H)RIHWESASLL(R) |
| 20803 - EW | M | 45 | Acute MI - STAGE 3 | CHF | 1211 | Complement C3f | (H)RIHWESASLL(R) |
| 23421 - FB | M | 59 | STAGE 3 | CHF | 1211 | Complement C3f | (H)RIHWESASLL(R) |
| 22813 - CL | F | 66 | STAGE 4 | CHF | 1211 | Complement C3f | (H)RIHWESASLL(R) |
| 23130 - ER | M | 51 | STAGE 3 | CHF | 1211 | Complement C3f | (H)RIHWESASLL(R) |
| 23105 - FC | M | 64 | STAGE 3 | CHF | 1211 | Complement C3f | (H)RIHWESASLL(R) |
| 23116 - FC | M | 59 | STAGE 3 | CHF | 1211 | Complement C3f | (H)RIHWESASLL(R) |
| 20414 - EYG | F | 76 | STAGE 3 | CHF | 1211 | Complement C3f | (H)RIHWESASLL(R) |
| 23130 - ER | M | 51 | STAGE 3 | CHF | 1211 | Complement C3f | (H)RIHWESASLL(R) |
| 23134 - FC | M | 62 | STAGE 3 | CHF | 1211 | Complement C3f | (H)RIHWESASLL(R) |
| 20102 - EAB | M | 70 | STAGE 3 | CHF | 1211 | Complement C3f | (H)RIHWESASLL(R) |

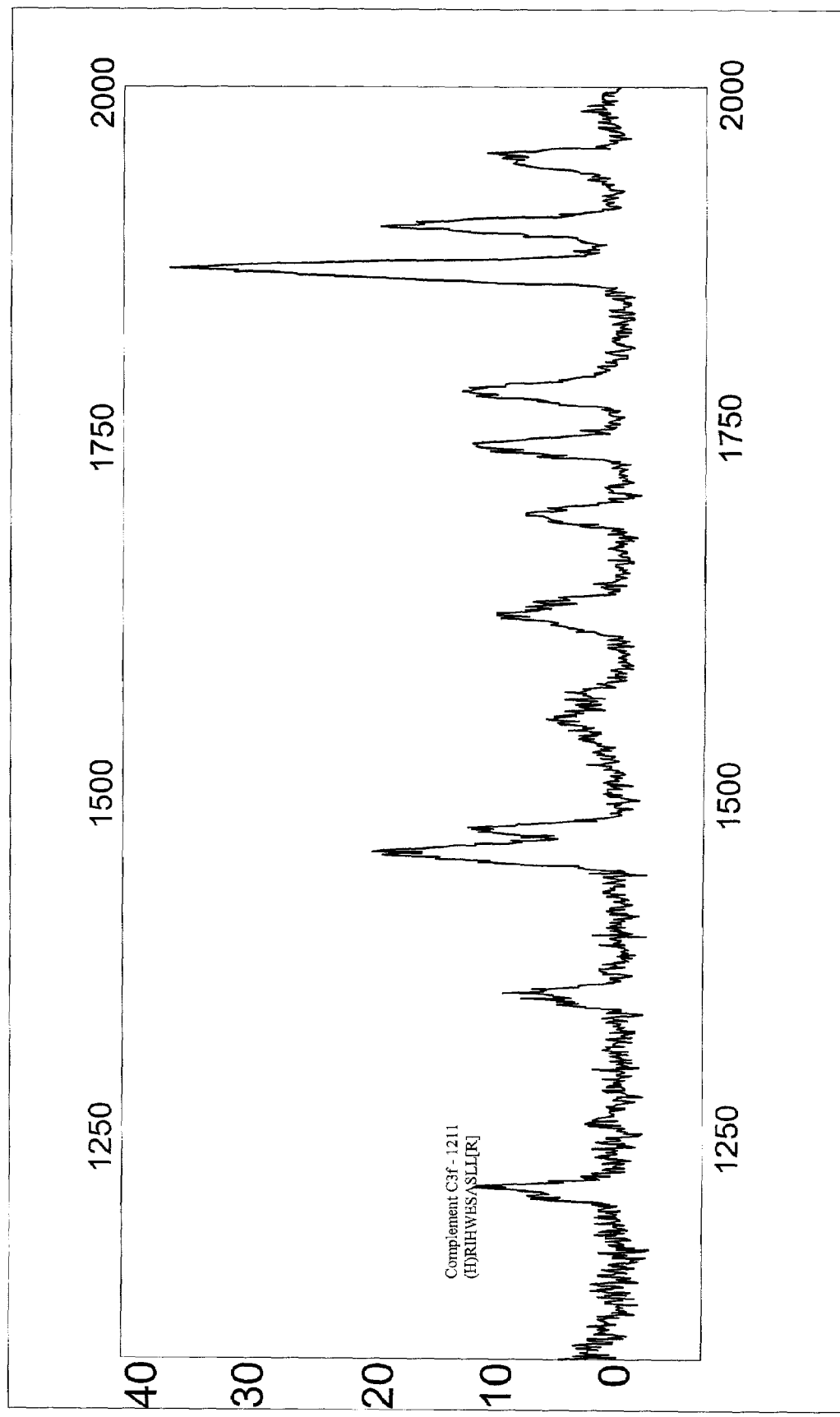

BIOPOLYMER MARKER INDICATIVE OF DISEASE STATE HAVING A MOLECULAR WEIGHT OF 1211 DALTONS

FIELD OF THE INVENTION

This invention relates to the field of characterizing the existence of a disease state; particularly to the utilization of mass spectroscopy to elucidate particular biopolymer markers indicative of disease state, and most particularly to specific biopolymer sequences having a unique relationship to at least one particular disease state.

BACKGROUND OF THE INVENTION

Methods utilizing mass spectrometry for the analysis of a target polypeptide have been taught wherein the polypeptide is first solubilized in an appropriate solution or reagent system. The type of solution or reagent system, e.g., comprising an organic or inorganic solvent, will depend on the properties of the polypeptide and the type of mass spectrometry performed and are well known in the art (see, e.g., Vorm et al. (1994) Anal. Chem. 66:3281 (for MALDI) and Valaskovic et al. (1995) Anal. Chem. 67:3802 (for ESI). Mass spectrometry of peptides is further disclosed, e.g., in WO 93/24834 by Chait et al.

In one prior art embodiment, the solvent is chosen so that the risk that the molecules may be decomposed by the energy introduced for the vaporization process is considerably reduced, or even fully excluded. This can be achieved by embedding the sample in a matrix, which can be an organic compound, e.g., sugar, in particular pentose or hexose, but also polysaccharides such as cellulose. These compounds are decomposed thermolytically into $CO_2$ and $H_2O$ so that no residues are formed which might lead to chemical reactions. The matrix can also be an inorganic compound, e.g., nitrate of ammonium which is decomposed practically without leaving any residues. Use of these and other solvents are further disclosed in U.S. Pat. No. 5,062,935 by Schlag et al.

Prior art mass spectrometer formats for use in analyzing the translation products include ionization (I) techniques, including but not limited to matrix assisted laser desorption (MALDI), continuous or pulsed electrospray (ESI) and related methods (e.g., IONSPRAY or THERMOSPRAY), or massive cluster impact (MCI); these ion sources can be matched with detection formats including linear or non-linear reflection time-off-flight (TOF), single or multiple quadropole, single or multiple magnetic sector, Fourier Transform ion cyclotron resonance (FTICR), ion trap, and combinations thereof (e.g., ion-trap/time-of-flight). For ionization, numerous matrix/wavelength combinations (MALDI) or solvent combinations (ESI) can be employed. Subattomole levels of protein have been detected, for example, using ESI (Valaskovic, G. A. et al., (1996) Science 273:1199–1202) or MALDI (Li, L. et al., (1996) J. Am. Chem. Soc. 118:1662–1663) mass spectrometry.

ES mass spectrometry has been introduced by Fenn et al. (J. Phys. Chem. 88, 4451–59 (1984); PCT Application No. WO 90/14148) and current applications are summarized in recent review articles (R. D. Smith et al., Anal. Chem. 62, 882–89 (1990) and B. Ardrey, Electrospray Mass Spectrometry, Spectroscopy Europe, 4, 10–18 (1992)). MALDI-TOF mass spectrometry has been introduced by Hillenkamp et al. ("Matrix Assisted UV-Laser Desorption/Ionization: A New Approach to Mass Spectrometry of Large Biomolecules," Biological Mass Spectrometry (Burlingame and McCloskey, editors), Elsevier Science Publishers, Amsterdam, pp. 49–60, 1990). With ESI, the determination of molecular weights in femtomole amounts of sample is very accurate due to the presence of multiple ion peaks which all could be used for the mass calculation.

The mass of the target polypeptide determined by mass spectrometry is then compared to the mass of a reference polypeptide of known identity. In one embodiment, the target polypeptide is a polypeptide containing a number of repeated amino acids directly correlated to the number of trinucleotide repeats transcribed/translated from DNA; from its mass alone the number of repeated trinucleotide repeats in the original DNA which coded it, may be deduced.

U.S. Pat. No. 6,020,208 utilizes a general category of probe elements (i.e., sample presenting means) with Surfaces Enhanced for Laser Desorption/Ionization (SELDI), within which there are three (3) separate subcategories. The SELDI process is directed toward a sample presenting means (i.e., probe element surface) with surface-associated (or surface-bound) molecules to promote the attachment (tethering or anchoring) and subsequent detachment of tethered analyte molecules in a light-dependent manner, wherein the said surface molecule(s) are selected from the group consisting of photoactive (photolabile) molecules that participate in the binding (docking, tethering, or crosslinking) of the analyte molecules to the sample presenting means (by covalent attachment mechanisms or otherwise).

PCT/EP97/04396 (WO 98/07036) teaches a process for determining the status of an organism by peptide measurement. The reference teaches the measurement of peptides in a sample of the organism which contains both high and low molecular weight peptides and acts as an indicator of the organism's status. The reference concentrates on the measurement of low molecular weight peptides, i.e. below 30,000 Daltons, whose distribution serves as a representative cross-section of defined controls. Contrary to the methodology of the instant invention, the '396 patent strives to determine the status of a healthy organism, i.e. a "normal" and then use this as a reference to differentiate disease states. The present inventors do not attempt to develop a reference "normal", but rather strive to specify particular markers which are evidentiary of at least one specific disease state, whereby the presence of said marker serves as a positive indicator of disease. This leads to a simple method of analysis which can easily be performed by an untrained individual, since there is a positive correlation of data. On the contrary, the '396 patent requires a complicated analysis by a highly trained individual to determine disease state versus the perception of non-disease or normal physiology.

Richter et al, Journal of Chromatography B, 726(1999) 25–35, refer to a database established from human hemofiltrate comprised of a mass database and a sequence database. The goal of Richter et al was to analyze the composition of the peptide fraction in human blood. Using MALDI-TOF, over 20,000 molecular masses were detected representing an estimated 5,000 different peptides. The conclusion of the study was that the hemofiltrate (HF) represented the peptide composition of plasma. No correlation of peptides with relation to normal and/or disease states is made.

As used herein, "analyte" refers to any atom and/or molecule; including their complexes and fragment ions. In the case of biological molecules/macromolecules or "biopolymers", such analytes include but are not limited to: proteins, peptides, DNA, RNA, carbohydrates, steroids, and lipids. Note that most important biomolecules under investigation for their involvement in the structure or regulation of life processes are quite large (typically several thousand times larger than $H_2O$.

As used herein, the term "molecular ions" refers to molecules in the charged or ionized state, typically by the addition or loss of one or more protons ($H^+$).

As used herein, the term "molecular fragmentation" or "fragment ions" refers to breakdown products of analyte molecules caused, for example, during laser-induced desorption (especially in the absence of added matrix).

As used herein, the term "solid phase" refers to the condition of being in the solid state, for example, on the probe element surface.

As used herein, "gas" or "vapor phase" refers to molecules in the gaseous state (i.e., in vacuo for mass spectrometry).

As used herein, the term "analyte desorption/ionization" refers to the transition of analytes from the solid phase to the gas phase as ions. Note that the successful desorption/ionization of large, intact molecular ions by laser desorption is relatively recent (circa 1988)—the big breakthrough was the chance discovery of an appropriate matrix (nicotinic acid).

As used herein, the term "gas phase molecular ions" refers to those ions that enter into the gas phase. Note that large molecular mass ions such as proteins (typical mass=60,000 to 70,000 times the mass of a single proton) are typically not volatile (i.e., they do not normally enter into the gas or vapor phase). However, in the procedure of the present invention, large molecular mass ions such as proteins do enter the gas or vapor phase.

As used herein in the case of MALDI, the term "matrix" refers to any one of several small, acidic, light absorbing chemicals (e.g., nicotinic or sinapinic acid) that is mixed in solution with the analyte in such a manner so that, upon drying on the probe element, the crystalline matrix-embedded analyte molecules are successfully desorbed (by laser irradiation) and ionized from the solid phase (crystals) into the gaseous or vapor phase and accelerated as intact molecular ions. For the MALDI process to be successful, analyte is mixed with a freshly prepared solution of the chemical matrix (e.g., 10,000:1 matrix:analyte) and placed on the inert probe element surface to air dry just before the mass spectrometric analysis. The large fold molar excess of matrix, present at concentrations near saturation, facilitates crystal formation and entrapment of analyte.

As used herein, "energy absorbing molecules (EAM)" refers to any one of several small, light absorbing chemicals that, when presented on the surface of a probe, facilitate the neat desorption of molecules from the solid phase (i.e., surface) into the gaseous or vapor phase for subsequent acceleration as intact molecular ions. The term EAM is preferred, especially in reference to SELDI. Note that analyte desorption by the SELDI process is defined as a surface-dependent process (i.e., neat analyte is placed on a surface composed of bound EAM). In contrast, MALDI is presently thought to facilitate analyte desorption by a volcanic eruption-type process that "throws" the entire surface into the gas phase. Furthermore, note that some EAM when used as free chemicals to embed analyte molecules as described for the MALDI process will not work (i.e., they do not promote molecular desorption, thus they are not suitable matrix molecules).

As used herein, "probe element" or "sample presenting device" refers to an element having the following properties: it is inert (for example, typically stainless steel) and active (probe elements with surfaces enhanced to contain EAM and/or molecular capture devices).

As used herein, "MALDI" refers to Matrix-Assisted Laser Desorption/Ionization.

As used herein, "TOF" stands for Time-of-Flight.

As used herein, "MS" refers to Mass Spectrometry.

As used herein "MALDI-TOF MS" refers to Matrix-assisted laser desorption/ionization time-of-flight mass spectrometry.

As used herein, "ESI" is an abbreviation for Electrospray ionization.

As used herein, "chemical bonds" is used simply as an attempt to distinguish a rational, deliberate, and knowledgeable manipulation of known classes of chemical interactions from the poorly defined kind of general adherence observed when one chemical substance (e.g., matrix) is placed on another substance (e.g., an inert probe element surface).

Types of defined chemical bonds include electrostatic or ionic (+/−) bonds (e.g., between a positively and negatively charged groups on a protein surface), covalent bonds (very strong or "permanent" bonds resulting from true electron sharing), coordinate covalent bonds (e.g., between electron donor groups in proteins and transition metal ions such as copper or iron), and hydrophobic interactions (such as between two noncharged groups).

As used herein, "electron donor groups" refers to the case of biochemistry, where atoms in biomolecules (e.g, N, S, O) "donate" or share electrons with electron poor groups (e.g., Cu ions and other transition metal ions).

With the advent of mass spectroscopic methods such as MALDI and SELDI, researchers have begun to utilize a tool that holds the promise of uncovering countless biopolymers which result from translation, transcription and post-translational transcription of proteins from the entire genome.

Operating upon the principles of retentate chromatography, SELDI MS involves the adsorption of proteins, based upon their physico-chemical properties at a given pH and salt concentration, followed by selectively desorbing proteins from the surface by varying pH, salt, or organic solvent concentration. After selective desorption, the proteins retained on the SELDI surface, the "chip", can be analyzed using the CIPHERGEN protein detection system, or an equivalent thereof. Retentate chromatography is limited, however, by the fact that if unfractionated body fluids, e.g. blood, blood products, urine, saliva, and the like, along with tissue samples, are applied to the adsorbent surfaces, the biopolymers present in the greatest abundance will compete for all the available binding sites and thereby prevent or preclude less abundant biopolymers from interacting with them, thereby reducing or eliminating the diversity of biopolymers which are readily ascertainable.

If a process could be devised for maximizing the diversity of biopolymers discernable from a sample, the ability of researchers to accurately determine the relevance of such biopolymers with relation to one or more disease states would be immeasurably enhanced.

SUMMARY OF THE INVENTION

The instant invention is characterized by the use of a combination of preparatory steps in conjunction with SELDI mass spectroscopy and time-of-flight detection procedures to maximize the diversity of biopolymers which are verifiable within a particular sample. The cohort of biopolymers verified within a sample is then viewed with reference to their ability to evidence at least one particular disease state; thereby enabling a diagnostician to gain the ability to characterize either the presence or absence of said at least one disease state relative to recognition of the presence and/or the absence of said biopolymer.

Although all manner of biomarkers related to all disease conditions are deemed to be within the purview of the instant invention and methodology, particular significance was given to those markers and diseases associated with the complement system and Syndrome X and diseases related thereto.

The complement system is an important part of non-clonal or innate immunity that collaborates with acquired immunity to destroy invading pathogens and to facilitate the clearance of immune complexes from the system. This system is the major effector of the humoral branch of the immune system, consisting of nearly 30 serum and membrane proteins. The proteins and glycoproteins composing the complement system are synthesized largely by liver hepatocytes. Activation of the complement system involves a sequential enzyme cascade in which the proenzyme product of one step becomes the enzyme catalyst of the next step. Complement activation can occur via two pathways: the classical and the alternative. The classical pathway is commonly initiated by the formation of soluble antigen-antibody complexes or by the binding of antibody to antigen on a suitable target, such as a bacterial cell. The alternative pathway is generally initiated by various cell-surface constituents that are foreign to the host. Each complement component is designated by numerals (C1–C9), by letter symbols, or by trivial names. After a component is activated, the peptide fragments are denoted by small letters. The complement fragments interact with one another to form functional complexes. Ultimately, foreign cells are destroyed through the process of a membrane-attack complex mediated lysis.

The C4 component of the complement system is involved in the classical activation pathway. It is a glycoprotein containing three polypeptide chains ($\alpha$, $\beta$, and $\gamma$). C4 is a substrate of component C1s and is activated when C1s hydrolyzes a small fragment (C4a) from the amino terminus of the $\alpha$ chain, exposing a binding site on the larger fragment (C4b).

The native C3 component consists of two polypeptide chains, $\alpha$ and $\beta$. As a serum protein, C3 is involved in the alternative pathway. Serum C3, which contains an unstable thioester bond, is subject to slow spontaneous hydrolysis into C3a and C3b. The C3f component is involved in the regulation required of the complement system which confines the reaction to designated targets. During the regulation process, C3b is cleaved into two parts: C3bi and C3f. C3bi is a membrane-bound intermediate wherein C3f is a free diffusible (soluble) component.

Complement components have been implicated in the pathogenesis of several disease conditions. C3 deficiencies have the most severe clinical manifestations, such as recurrent bacterial infections and immune-complex diseases, reflecting the central role of C3. The rapid profusion of C3f moieties and resultant "accidental" lysis of normal cells mediated thereby gives rise to a host of auto-immune reactions. The ability to understand and control these mechanisms, along with their attendant consequences, will enable practitioners to develop both diagnostic and therapeutic avenues by which to thwart these maladies.

In the course of defining a plurality of disease specific marker sequences, special significance was given to markers which were evidentiary of a particular disease state or with conditions associated with Syndrome-X. Syndrome-X is a multifaceted syndrome, which occurs frequently in the general population. A large segment of the adult population of industrialized countries develops this metabolic syndrome, produced by genetic, hormonal and lifestyle factors such as obesity, physical inactivity and certain nutrient excesses. This disease is characterized by the clustering of insulin resistance and hyperinsulinemia, and is often associated with dyslipidemia (atherogenic plasma lipid profile), essential hypertension, abdominal (visceral) obesity, glucose intolerance or noninsulin-dependent diabetes mellitus and an increased risk of cardiovascular events. Abnormalities of blood coagulation (higher plasminogen activator inhibitor type I and fibrinogen levels), hyperuricemia and microalbuminuria have also been found in metabolic syndrome-X.

The instant inventors view the Syndrome X continuum in its cardiovascular light, while acknowledging its important metabolic component. The first stage of Syndrome X consists of insulin resistance, abnormal blood lipids (cholesterol and triglycerides), obesity, and high blood pressure (hypertension). Any one of these four first stage conditions signals the start of Syndrome X.

Each first stage Syndrome X condition risks leading to another. For example, increased insulin production is associated with high blood fat levels, high blood pressure, and obesity. Furthermore, the effects of the first stage conditions are additive; an increase in the number of conditions causes an increase in the risk of developing more serious diseases on the Syndrome X continuum.

A patient who begins the Syndrome X continuum risks spiraling into a maze of increasingly deadly diseases. The next stages of the Syndrome X continuum lead to overt diabetes, kidney failure, and heart failure, with the possibility of stroke and heart attack at any time. Syndrome X is a dangerous continuum, and preventative medicine is the best defense. Diseases are currently most easily diagnosed in their later stages, but controlling them at a late stage is extremely difficult. Disease prevention is much more effective at an earlier stage.

Subsequent to the isolation of particular disease state marker sequences as taught by the instant invention, the promulgation of various forms of risk-assessment tests are contemplated which will allow physicians to identify asymptomatic patients before they suffer an irreversible event as diabetes, kidney failure, and heart failure, and enable effective disease management and preventative medicine. Additionally, the specific diagnostic tests which evolve from this methodology provide a tool for rapidly and accurately diagnosing acute Syndrome X events such as heart attack and stroke, and facilitate treatment.

Accordingly, it is an objective of the instant invention to define a disease specific marker sequence which is useful in evidencing and categorizing at least one particular disease state.

It is another objective of the instant invention to evaluate samples containing a plurality of biopolymers for the presence of disease specific marker sequences which evidence a link to at least one specific disease state.

It is a further objective of the instant invention to elucidate essentially all biopolymeric moieties contained therein, whereby particularly significant moieties may be identified.

It is a further objective of the instant invention provide at least one purified antibody which is specific to said disease specific marker sequence.

It is yet another objective of the instant invention to teach a monoclonal antibody which is specific to said disease specific marker sequence.

It is a still further objective of the invention to teach polyclonal antibodies raised against said disease specific marker.

It is yet an additional objective of the instant invention to teach a diagnostic kit for determining the presence of said disease specific marker.

It is a still further objective of the instant invention to teach methods for characterizing disease state based upon the identification of said disease specific marker.

Other objectives and advantages of this invention will become apparent from the following description taken in conjunction with the accompanying drawings wherein are set forth, by way of illustration and example, certain embodiments of this invention. The drawings constitute a part of this specification and include exemplary embodiments of the present invention and illustrate various objects and features thereof.

BRIEF DESCRIPTION OF THE FIGURES

FIG. 1 is a representation of derived data which characterizes a disease specific marker having a particular sequence (SEQ ID NO:1) useful in evidencing and categorizing at least one particular disease state. Each patient listed in the data table shows the presence of SEQ ID NO:1 in their serum.

FIGS. 2A and 2B show alternative representations of the characteristic profile derived via SELDI/TOF MS of the disease specific marker of FIG. 1 (SEQ ID NO:1).

DETAILED DESCRIPTION OF THE INVENTION

Serum samples from individuals were analyzed using Surface Enhanced Laser Desorption Ionization (SELDI) using the Ciphergen PROTEINCHIP system. The chip surfaces included, but were not limited to IMAC-3-Ni, SAX2 surface chemistries, gold chips, and the like.

Preparatory to the conduction of the SELDI MS procedure, various preparatory steps were carried out in order to maximize the diversity of discernible moieties from the sample. Utilizing a type of micro-chromatographic column called a C18-ZIPTIP available from the Millipore company, the following preparatory steps were conducted.
 1. Dilute sera in sample buffer;
 2. Aspirate and dispense ZIP TIP in 50% Acetonitrile;
 3. Aspirate and dispense ZIP TIP in Equilibration; solution;
 4. Aspirate and Dispense in serum sample;
 5. Aspirate and Dispense ZIP TIP in Wash solution;
 6. Aspirate and Dispense ZIP TIP in Elution Solution.

Illustrative of the various buffering compositions useful in the present invention are:

Sample Buffers (various low pH's): Hydrochloric acid (HCl), Formic acid, Trifluoroacetic acid (TFA), Equilibration Buffers (various low pH's): HC, Formic acid, TFA;

Wash Buffers (various low pH's): HCl, Formic acid, TFA;

Elution Solutions (various low pH's and % Solvents): HCl, Formic acid, TFA;

Solvents: Ethanol, Methanol, Acetonitrile.

Spotting was then Performed, for Example upon a Gold Chip in the Following Manner:
 1. spot 2 ul of sample onto each spot
 2. let sample partially dry
 3. spot 1 ul of matrx, and let air dry.

HiQ Anion Exchange Mini Column Protocol
 1. Dilute sera in sample/running buffer;
 2. Add HiQ resin to column and remove any air bubbles;
 3. Add Uf water to aid in column packing;
 4. Add sample/running buffer to equilibrate column;
 5. Add diluted sera;
 6. Collect all the flow through fraction in Eppendorf tubes until level is at resin;
 7. Add sample/running buffer to wash column;
 8. Add elusion buffer and collect elusion in Eppendorf tubes.

Illustrative of the various buffering compositions useful in this technique are:

Sample/Running buffers: including but not limited to Bicine buffers of various molarities, pH's, NaCl content, Bis-Tris buffers of various molarities, pH's, NaCl content, Diethanolamine of various molarities, pH's, NaCl content, Diethylamine of various molarities, pH's, NaCl content, Imidazole of various molarities, pH's, NaCl content, Tricine of various molarities, pH's, NaCl content, Triethanolamine of various molarities, pH's, NaCl content, Tris of various molarities, pH's, NaCl content.

Elution Buffer: Acetic acid of various molarities, pH's, NaCl content, Citric acid of various molarities, pH's, NaCl content, HEPES of various molarities, pH's, NaCl content, MES of various molarities, pH's, NaCl content, MOPS of various molarities, pH's, NaCl content, PIPES of various molarities, pH's, NaCl content, Lactic acid of various molarities, pH's, NaCl content, Phosphate of various molarities, pH's, NaCl content, Tricine of various molarities, pH's, NaCl content.

Chelating SEPHAROSE Mini Column
 1. Dilute Sera in Sample/Running buffer;
 2. Add Chelating SEPHAROSE slurry to column and allow column to pack:
 3. Add UF water to the column to aid in packing;
 4. Add Charging Buffer once water is at the level of the resin surface;
 5. Add UF water to wash through non bound metal ions once charge buffer washes through;
 6. Add running buffer to equilibrate column for sample loading;
 7. Add diluted serum sample;
 8. Add running buffer to wash unbound protein;
 9. Add elution buffer and collect elution fractions for analysis;
 10. Acidify each elution fraction.

Illustrative of the various buffering compositions useful in this technique are: Sample/Running buffers including but not limited to Sodium Phosphate buffers at various molarities and pH's;

Charging buffers including but not limited to Nickel Chloride, Nickel Sulphate, Copper II Chloride, Zinc Chloride or any suitable metal ion solution;

Elution Buffers including but not limited to Sodium phosphate buffers at various molarities and pH's containing various molarities of EDTA and/or Imidazole.

HiS Cation Exchange Mini Column Protocol
 1. Dilute sera in sample/running buffer;
 2. Add HiS resin to column and remove any air bubbles;
 3. Add Uf water to aid in column packing;
 4. Add sample/running buffer to equilibrate column for sample loading;
 5. Add diluted sera to column;
 6. Collect all flow through fractions in Eppendorf tubes until level is at resin.

7. Add sample/running buffer to wash column.

8. Add elusion buffer and collect elusion in Eppendorf tubes.

Illustrative of the various buffering compositions useful in this technique are:

Sample/Running buffers: including but not limited to Bicine buffers of various molarities, pH's, NaCl content, Bis-Tris buffers of various molarities, pH's, NaCl content, Diethanolamine of various molarities, pH's, NaCl content, Diethylamine of various molarities, pH's, NaCl content, Imidazole of various molarities, pH's, NaCl content, Tricine of various molarities, pH's, NaCl content, Triethanolamine of various molarities, pH's, NaCl content, Tris of various molarities, pH's, NaCl content.

Elution Buffer: Acetic acid of various molarities, pH's, NaCl content, Citric acid of various molarities, pH's, NaCl content, HEPES of various molarities, pH's, NaCl content, MES of various molarities, pH's, NaCl content, MOPS of various molarities, pH's, NaCl content, PIPES of various molarities, pH's, NaCl content, Lactic acid of various molarities, pH's, NaCl content, Phosphate of various molarities, pH's, NaCl content, Tricine of various molarities, pH's, NaCl content.

The procedure for profiling serum samples is described below:

Following the preparatory steps illustrated above, various methods for use of the PROTEINCHIP arrays, available for purchase from Ciphergen Biosystems (Palo Alto, Calif., may be practiced. Illustrative of one such method is as follows.

The first step involved treatment of each spot with 20 ml of a solution of 0.5 M EDTA for 5 minutes at room temperature in order to remove any contaminating divalent metal ions from the surface. This was followed by rinsing under a stream of ultra-filtered, deionized water to remove the EDTA. The rinsed surfaces were treated with 20 ml of 100 mM Nickel sulfate solution for 5 minutes at room temperature after which the surface was rinsed under a stream of ultra-filtered, deionized water and allowed to air dry.

Serum samples (2 ml) were applied to each spot (now "charged" with the metal-Nickel) and the PROTEINCHIP was returned to the plastic container in which it was supplied. A piece of moist KIMWIPE was placed at the bottom of the container to generate a humid atmosphere. The cap on the plastic tube was replaced and the chip allowed to incubate at room temperature for one hour. At the end of the incubation period, the chip was removed from the humid container and washed under a stream of ultra-filtered, deionized water and allowed to air dry. The chip surfaces (spots) were now treated with an energy-absorbing molecule that helps in the ionization of the proteins adhering to the spots for analysis by Mass Spectrometry. The energy-absorbing molecule in this case was sinapinic acid and a saturated solution prepared in 50% acetonitrile and 0.05% TFA was applied (1 ml) to each spot. The solution was allowed to air dry and the chip analyzed immediately using MS (SELDI).

Serum samples from patients suffering from a variety of disease states were analyzed using one or more protein chip surfaces, e.g. a gold chip or an IMAC nickel chip surface as described above and the profiles were analyzed to discern notable sequences which were deemed in some way evidentiary of at least one disease state.

In order to purify the disease specific marker and further characterize the sequence thereof, additional processing was performed.

For example, Serum (20 ml) was (diluted 5-fold with phosphate buffered saline) concentrated by centrifugation through a YM3 MICROCON spin filter (Amicon) for 20 min at 10,000 RPM at 4° C. in a Beckman MICROCENTRIFuge R model bench top centrifuge. The filtrate was discarded and the retained solution, which contained the two peptides of interest, was analyzed further by tandem mass spectrometry to deduce their amino acid sequences. Tandem mass spectrometry was performed at the University of Manitoba's (Winnipeg, Manitoba, Canada) mass spectrometry laboratory using the procedures that are well known to practitioners of the art.

As a result of these procedures, the disease specific marker identified as SEQ ID NO:1 was found. This marker is characterized as a C3f fragment from the complement system having a molecular weight of about 1211 daltons. The characteristic profile of the marker is set forth in the representations in FIGS. 2A and 2B. As easily deduced from the data set forth in FIG. 1, this marker is indicative of an individual suffering from myocardial infarction, intracerebral hemorrhage or congestive heart failure.

In accordance with various stated objectives of the invention, the skilled artisan, in possession of the specific disease specific marker as instantly disclosed, would readily carry out known techniques in order to raise purified biochemical materials, e.g. monoclonal and/or polyclonal antibodies, which are useful in the production of methods and devices useful as point-of-care rapid assay diagnostic or risk assessment devices as are known in the art.

The specific disease markers which are analyzed according to the method of the invention are released into the circulation and may be present in the blood or in any blood product, for example plasma, serum, cytolyzed blood, e.g. by treatment with hypotonic buffer of detergents and dilutions and preparations thereof, and other body fluids, e.g. cerebrospinal fluid (CSF), saliva, urine, lymph, and the like. The presence of each marker is determined using antibodies specific for each of the markers and detecting specific binding of each antibody to its respective marker. Any suitable direct or indirect assay method may be used to determine the level of each of the specific markers measured according to the invention. The assays may be competitive assays, sandwich assays and the label may be selected from the group of well-known labels such as radioimmunoassay, fluorescent, or chemiluminescence immunoassay or immunoPCR technology. Extensive discussion of the known immunoassay techniques is not required here since these are known to those of skill in the art. See Takahashi et al. (Clin Chem 1999; 45(8) : 1307) for S100B assay.

A monoclonal antibody specific against the disease marker sequence isolated by the present invention may be produced, for example, by the polyethylene glycol (PEG) mediated cell fusion method, in a manner well-known in the art.

Traditionally, monoclonal antibodies have been made according to fundamental principles laid down by Kohler and Milstein. Mice are immunized with antigens, with or without, adjuvants. The splenocytes are harvested from the spleen for fusion with immortalized hybridoma partners. These are seeded into microtitre plates where they can secrete antibodies into the supernatant that is used for cell culture. To select from the hybridomas that have been plated for the ones that produce antibodies of interest the hybridoma supernatants are usually tested for antibody binding to antigens in an ELISA (enzyme linked immunosorbent assay) assay. The idea is that the wells that contain the hybridoma of interest will contain antibodies that will bind most avidly to the test antigen, usually the immunizing antigen. These wells are then subcloned in limiting dilution fashion to produce monoclonal hybridomas. The selection for the clones of interest is repeated using an ELISA assay to test for antibody binding. Therefore, the principle that has been propagated is that in the production of monoclonal antibodies the hybridomas that produce the most avidly binding antibodies are the ones that are selected from among all the hybridomas that were initially produced. That is to say, the preferred antibody is the one with highest affinity for the antigen of interest.

There have been many modifications of this procedure such as using whole cells for immunization. In this method, instead of using purified antigens, entire cells are used for immunization. Another modification is the use of cellular ELISA for screening. In this method instead of using purified antigens as the target in the ELISA, fixed cells are used. In addition to ELISA tests, complement mediated cytotoxicity assays have also been used in the screening process. However, antibody-binding assays were used in conjunction with cytotoxicity tests. Thus, despite many modifications, the process of producing monoclonal antibodies relies on antibody binding to the test antigen as an endpoint.

The purified monoclonal antibody is utilized for immunochemical studies.

Polyclonal antibody production and purification utilizing one or more animal hosts in a manner well-known in the art can be performed by a skilled artisan.

Another objective of the present invention is to provide reagents for use in diagnostic assays for the detection of the particularly isolated disease specific marker sequences of the present invention.

In one mode of this embodiment, the marker sequences of the present invention may be used as antigens in immunoassays for the detection of those individuals suffering from the disease known to be evidenced by said marker sequence. Such assays may include but are not limited to: radioimmunoassay, enzyme-linked immunosorbent assay (ELISA), "sandwich" assays, precipitin reactions, gel diffusion immunodiffusion assay, agglutination assay, fluorescent immunoassays, protein A or G immunoassays and immunoelectrophoresis assays.

According to the present invention, monoclonal or polyclonal antibodies produced against the disease specific marker sequence of the instant invention are useful in an immunoassay on samples of blood or blood products such as serum, plasma or the like, spinal fluid or other body fluid, e.g. saliva, urine, lymph, and the like, to diagnose patients with the characteristic disease state linked to said marker sequence. The antibodies can be used in any type of immunoassay. This includes both the two-site sandwich assay and the single site immunoassay of the non-competitive type, as well as in traditional competitive binding assays.

Particularly preferred, for ease and simplicity of detection, and its quantitative nature, is the sandwich or double antibody assay of which a number of variations exist, all of which are contemplated by the present invention. For example, in a typical sandwich assay, unlabeled antibody is immobilized on a solid phase, e.g. microtiter plate, and the sample to be tested is added. After a certain period of incubation to allow formation of an antibody-antigen complex, a second antibody, labeled with a reporter molecule capable of inducing a detectable signal, is added and incubation is continued to allow sufficient time for binding with the antigen at a different site, resulting with a formation of a complex of antibody-antigen-labeled antibody. The presence of the antigen is determined by observation of a signal which may be quantitated by comparison with control samples containing known amounts of antigen.

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and drawings/figures.

One skilled in the art will readily appreciate that the present invention is well adapted to carry out the objectives and obtain the ends and advantages mentioned, as well as those inherent therein. The oligonucleotides, peptides, polypeptides, biologically related compounds, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An isolated biopolymer marker peptide consisting of amino acid residues 2–11 of SEQ ID NO:1 diagnostic for myocardial infarction, congestive heart failure or intracerebral hemorrhage.

2. A method for diagnosing myocardial infarction, congestive heart failure or intracerebral hemorrhage comprising:
  (a) obtaining a sample from a patient;
  (b) preparing said sample to maximize the diversity of biopolymers discernible from said sample;
  (c) conducting mass spectrometric analysis on said sample; and
  (d) comparing mass spectrum profiles of a peptide consisting of amino acid residues 2–11 of SEQ ID NO:1 to mass spectrum profiles of biopolymers discerned from said sample; wherein recognition of a mass spectrum profile in the sample displaying the characteristic profile of the mass spectrum profile for the peptide consisting of amino acid residues 2–11 of SEQ ID NO:1 is diagnostic for myocardial infarction, congestive heart failure or intracerebral hemorrhage.

3. The method of claim 2, wherein the sample is an unfractionated body fluid or a tissue sample.

4. The method of claim 2, wherein said sample is selected from the group consisting of blood, blood products, urine, saliva, cerebrospinal fluid, and lymph.

5. The method of claim 2, wherein said mass spectrometric analysis is Surface Enhanced Laser Desorption Ionization (SELDI) mass spectrometry (MS).

6. The method of claim 2, wherein said patient is a human.

7. A kit for determining the presence of an isolated biopolymer marker peptide consisting of amino acid residues 2–11 of SEQ ID NO:1 comprising: (a) an isolated biopolymer marker peptide consisting of amino acid residues 2–11 of SEQ ID NO:1 and (b) an antibody that binds to said peptide in a sample from a patient.

8. The kit of claim 7, wherein said antibody is immobilized on a solid support.

9. The kit of claim 7, wherein said antibody is labeled.

* * * * *

SEQUENCE LISTING

<160> NUMBER OF SEQ ID NOS: 1

<210> SEQ ID NO 1
<211> LENGTH: 12
<212> TYPE: PRT
<213> ORGANISM: Homo sapiens

<400> SEQUENCE: 1

His Arg Ile His Trp Glu Ser Ala Ser Leu Leu Arg
1               5                   10